United States Patent
Cook et al.

(10) Patent No.: US 7,598,367 B2
(45) Date of Patent: *Oct. 6, 2009

(54) EARLY LIGHT-INDUCED PROTEIN PROMOTERS

(75) Inventors: Zhihong C. Cook, Woodland Hills, CA (US); Leonard Medrano, Azusa, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/408,791

(22) Filed: Apr. 21, 2006

(65) Prior Publication Data

US 2007/0006337 A1 Jan. 4, 2007

Related U.S. Application Data

(63) Continuation-in-part of application No. 11/172,703, filed on Jun. 30, 2005, now Pat. No. 7,214,789.

(51) Int. Cl.
  *C07H 21/04* (2006.01)
  *C12N 15/87* (2006.01)
  *A01H 11/00* (2006.01)
  *C12N 15/00* (2006.01)

(52) U.S. Cl. .................. 536/24.1; 435/320.1; 435/440; 800/278; 800/295; 800/298

(58) Field of Classification Search ........................ None
See application file for complete search history.

(56) References Cited

U.S. PATENT DOCUMENTS

| 4,668,777 | A | 5/1987 | Caruthers et al. |
| 5,380,831 | A | 1/1995 | Adang et al. |
| 5,436,391 | A | 7/1995 | Fujimoto et al. |
| 2007/0226830 | A1* | 9/2007 | Pennell et al. ............... 800/278 |

FOREIGN PATENT DOCUMENTS

| WO | 2006/005023 | 1/2006 |
| WO | 2007/011887 | 1/2007 |

OTHER PUBLICATIONS

U.S. Appl. No. 11/916,935, filed Dec. 2007, Park et al.*
Kimura, Yoshizumi, Manabe, Yamamoto and Matsui, in "Arabidopsis transcriptional regulation by light stress via hydrogen peroxide-dependent and -independent pathways" in Genes to Cells (2001) vol. 6, p. 607-617.*
GenBank locus AB022223, Feb. 12, 2004.*
Armaleo et al., "Biolistic nuclear transformation of *Saccharomyces cerevisiae* and other fungi" *Current Genetics*, 17:97 (1990).
Auch et al. "Exon Trap Cloning: Using PCR to Rapidly Detect and Clone Exons from Genomic DNA Fragments," *Nucleic Acids Research*, 18(22):6743 (1990).
Ballas et al. "Efficient functioning of plant promoters and poly(A) sites in Xenopus oocytes" *Nucleic Acids Research*, 17:7891-7903 (1989).
Beaucage et al. "Deoxynucleoside phosphoramidites—a new class of key intermediates for deoxypolynucleotide synthesis" *Tet. Lett.* 22:1859-1862 (1981).
Bouvier et al. "Induction and Control of Chromoplast-specific Carotenoid Genes by Oxidative Stress" *J. Biol. Chem.*, 273:30651-59 (1998).
Burke et al., "The DPE, a conserved downstream core promoter element that is functionally analogous to the TATA box" *Cold Spring Harb. Symp. Quant. Biol.*, 63:75-82 (1998).
Canton and Quail "Both phyA and phyB mediate light-imposed repression of PHYA gene expression in Arabidopsis" *Plant Physiol.* 121:1207-16 (1999).
Comai et al. "Expression in plants of a mutant *aroA* gene from *Salmonella typhimurium* confers tolerance to glyphosate" *Nature*, 317:741-744 (1985).
Escudero et al., "T-DNA transfer in meristematic cells of maize provided with intracellular *Agrobacterium*" *Plant J.* 10:355 (1996).
Farmer and Ryan "Interplant communication: airborne methyl jasmonate induces synthesis of proteinase inhibitors in plant leaves" *Proc. Natl. Acad. Sci. USA* 87:7713-7716 (1990).
Germain and Ricard "Two Idh genes from tomato and their expression in different organs, during fruit ripening and in response to stress" *Plant Mol. Biol.* 35:949-54 (1997).
Gordon-Kamm et al. "Transformation of maize cells and regeneration of fertile transgenic plants" *Plant Cell* 2:603-618 (1990).
Gruber et al., "Vectors for Plant Transformation" *Methods in Plant Molecular Biology & Biotechnology*, pp. 89-119 (1993).
Guerineau et al. "Effect of deletions in the cauliflower mosaic virus polyadenylation sequence on the choice of the polyadenylation sites in tobacco protoplasts" *Mol. Gen. Genet.*, 262:141-144 (1991).
Hensel et al. "Developmental and age-related processes that influence the longevity and senescence of photosynthetic tissues in Arabidopsis" *Plant Cell*, 5:553-64 (1993).
Herrera-Estrella et al., "Chimeric genes as dominant selectable markers in plant cells" *EMBO J.* 2:987 (1983).
Hirose et al. "cDNA cloning and tissue specific expression of a gene for sucrose transporter from rice (*Oryza sativa* L.)" *Plant Cell Physiol.* 38:1389-96 (1997).
Ho et al. "Site-directed mutagenesis by overlap extension using the polymerase chain reaction" *Gene*, 77:51-59 (1989).
Horsch et al. "A simple and general method for transferring genes into plants" *Science*, 227:1229 (1985).
Huang et al. "The Arabidopsis ACT11 actin gene is strongly expressed in tissues of the emerging inflorescence, pollen, and developing ovules" *Plant Mol. Biol.* 33:125-39 (1997).
Hwang and Goodman, "An *Arabidopsis thaliana* root-specific kinase homolog is induced by dehydration, ABA, and NaCl" *Plant J.* 8:37 (1995).

(Continued)

*Primary Examiner*—Nancy Vogel
*Assistant Examiner*—Catherine Hibbert
(74) *Attorney, Agent, or Firm*—Fish & Richardson P.C.

(57) ABSTRACT

The present invention is directed to promoter sequences and promoter control elements, polynucleotide constructs comprising the promoters and control elements, and methods of identifying the promoters, control elements, or fragments thereof. The invention further relates to the use of the present promoters or promoter control elements to modulate transcript levels.

3 Claims, No Drawings

OTHER PUBLICATIONS

Ishida et al., "High efficiency transformation of maize (*Zea mays* L.) mediated by *Agrobacterium tumefaciens*" *Nature Biotechnology* 14:745 (1996).

Jones et al. "Ethylene-regulated expression of a carnation cysteine proteinase during flower petal senescence" *Plant Mol. Biol.* 28:505-12 (1995).

Joshi et al. (1987) "An inspection of the domain between putative TATA box and translation start site in 79 plant genes" *Nucleic Acid Res.* 15:9627-9639.

Kalaitzis et al. "Cloning of a tomato polygalacturonase expressed in abscission" *Plant Mol. Biol.* 28:647-56(1995).

Kirch et al. "Structural organization, expression and promoter activity of a cold-stress-inducible gene of potato (*Solanum tuberosum* L.)" *Plant Mol. Biol.* 33:897-909 (1997).

Koltunow et al., "Different temporal and spatial gene expression patterns occur during another development" *Plant Cell*, 2:1201 (1990).

Kuster et al. "The sucrose synthase gene is predominantly expressed in the root nodule tissue of *Vicia faba* " *Mol. Plant Microbe Interact.* 6:507-14 (1993).

Lindsey et al. (1993) "Tagging Genomic Sequences That Direct Transgene Expression by Activation of a Promoter Trap in Plants," *Transgenic Research*, 2:3347.

Liu et al. "Rapid sequencing of unpurified PCR products by thermal asymmetric PCR cycle sequencing using unlabeled sequencing primers" *Nucl. Acids Res.* 21(14):3333-3334 (1993).

Liu et al. "Efficient isolation and mapping of *Arabidopsis thaliana* T-DNA insert junctions by thermal asymmetric interlaced PCR" *Plant J.* 8(3):457-463 (1995).

Liu et al. "Thermal asymmetric interlaced PCR: automatable amplification and sequencing of insert end fragments from P1 and YAC clones for chromosome walking" *Genomics*, 25:674-681 (1995).

Miki et al. "Procedures for Introducing Foreign DNA into Plants" *Methods in Plant Molecular Biology & Biotechnology*, pp. 67-88 (1993).

Marrs and Walbot "Expression and RNA splicing of the maize glutathione S-transferase Bronze2 gene is regulated by cadmium and other stresses" *Plant Physiol.* 113:93-102 (1997).

Mason and Mullet "Expression of two soybean vegetative storage protein genes during development and in response to water deficit, wounding, and jasmonic acid" *Plant Cell*, 2:569-579 (1990).

May et al., "Generation of transgenic banana (*Musa acuminate*) plants via *Agrobacterium*-Mediated transformation" *Bio/Technology*, 13:486 (1995).

Mogen et al. "Upstream sequences other than AAUAAA are required for efficient messenger RNA 3'-end formation in plants" *Plant Cell*, 2:1261-1272 (1990).

Montgomery et al. "Positive and negative regulatory regions control the spatial distribution of polygalacturonase transcription in tomato fruit pericarp" *The Plant Cell*, 5:1049-1062 (1993).

Munroe et al. "Tales of poly(A): a review" *Gene* 91:151-158 (1990).

Murray et al. "Codon usage in plant genes" *Nucleic Acids Res.* 17:477-498 (1989).

Needleman and Wunsch "A general method applicable to the search for similarities in the amino acid sequence of two proteins" *J. Mol. Biol.*, 48:443 (1970).

O'Donnell et al. "A novel tomato gene that rapidly responds to wound- and pathogen-related signals" *Plant J.*, 14(1):137-42 (1998).

Pearson and Lipman "Improved tools for biological sequence comparison" *Proc. Natl. Acad. Sci.* (USA) 85:2444 (1988).

Pena-Cortes et al. "Systemic induction of proteinase-inhibitor-II gene expression in potato plants by wounding" *Planta*, 174:84-89 (1988).

Pham-Thi et al. "Enzymatic activity and gene expression under water stress of phospholipase D in two cultivars of *Vigna unguiculata* L. Walp. differing in drought tolerance" *Plant Mol. Biol.* 1257-65 (1999).

Phillips et al. "Cell-Tissue Culture and In-Vitro Manipulation" *Corn & Corn Improvement*, 3rd Edition, *American Society of Agronomy Inc*, pp. 345-387 (1988).

Proudfoot "Poly(A) signals" *Cell*, 64:671-674 (1991).

Rea et al. "Developmentally and wound-regulated expression of the gene encoding a cell wall copper amine oxidase in chickpea seedlings" *FEBS Letters*, 437:177-82 (1998).

Reddy et al. "Cloning and characterization of a cDNA encoding topoisomerase II in pea and analysis of its expression in relation to cell proliferation" *Plant Mol. Biol.* 41:125-37 (1999).

Rivoal et al. "Differential induction of pyruvate decarboxylase subunits and transcripts in anoxic rice seedlings" *Plant Physiol.* 114(3):1021-29 (1997).

Rohde et al. "ABI3 affects plastid differentiation in dark-grown *Arabidopsis* seedlings" *Plant Cell*, 12:35-52 (2000).

Salomon et al. "Genetic identification of functions of TR-DNA transcripts in octopine crown galls" *EMBO J.*, 3:141 (1984).

Sambrook et al., *Molecular Cloning: A Laboratory Manual*, 2nd Ed. (1989) Cold Spring Harbor Press, Cold Spring Harbor, NY.

Sanfacon et al. "A dissection of the cauliflower mosaic virus polyadenylation signal" *Genes Dev.* 5:141-149 (1991).

Sessa et al. "Dark induction and subcellular localization of the pathogenesis-related PRB-1b protein" *Plant Mol. Biol.* 28:537-47 (1995).

Shani et al. "Cloning and characterization of elongation specific endo-1,4-beta-glucanase (cell) from *Arabidopsis thaliana* " *Plant Mol. Biol.* 34(6):837-42 (1997).

Smale, "Core promoter architecture for eukaryotic protein-coding genes" Transcription: Mechanisms and Regulation (eds. R.C. Conaway and J.W. Conaway), *Raven Press, Ltd.*, New York, pp. 63-81, 1994.

Smale, "Transcription initiation from TATA-less promoters within eukaryotic protein-coding genes" *Biochim. Biophys. Acta*, 1351:73-88, 1997.

Smale et al., "The initiator element: a paradigm for core promoter heterogeneity within metazoan protein-coding genes" *Cold Spring Harb. Symp. Quant. Biol.*, 58:21-31, 1998.

Smale, "Core promoters: active contributors to combinatorial gene regulation" *Genes & Dev.*, 15:2503-2508 (2001).

Smith and Waterman "Comparison of biosequences" *Adv. Appl. Math.*, 2:482 (1981).

Stalker et al. "Herbicide resistance in transgenic plants expressing a bacterial detoxification gene" *Science*, 242:(4877):419-423 (1988).

Stromvik et al. "A novel promoter from soybean that is active in a complex developmental pattern with and without its proximal 650 base pairs" *Plant Mol. Biol.* 41:217-31 (1999).

Struhl, "Promoters, activator proteins, and the mechanism of transcriptional initiation in yeast" *Cell*, 49:295-297 (1987).

Tomes et al., "16 direct DNA transfer into intact plant cells via microprojectile bombardment" Plant Cell, Tissue and Organ Culture: Fundamental Methods (Gamborg and Phillips eds.) *Springer Verlag*, Berlin (1995).

Tsai and Coruzzi, "Dark-induced and organ-specific expression of two asparagine synthetase genes in *Pisum sativum* " *EMBO J.* 9:323-32 (1990).

Vaucheret et al. "Transgene-induced gene silencing in plants" *Plant J.*, 16:651-659 (1998).

Vergunst et al. "Cre/lox-mediated site-specific integration of *Agrobacterium* T-DNA in *Arabidopsis thaliana* by transient expression of cre" *Plant Mol. Biol.* 38:393 (1998).

Walter et al. "Bean ribonuclease-like pathogenesis-related protein genes (Ypr10) display complex patterns of developmental, dark-induced and exogenous-stimulus-dependent expression" *Eur. J. Biochem.*, 239:281-93 (1996).

Weis and Reinberg, "Transcription by RNA polymerase II: initiator-directed formation of transcription-competent complexes" *FASEB J.* 6:3300-3309 (1992).

Wingender et al. "Differential regulation of soybean chalcone synthase genes in plant defence, symbiosis and upon environmental stimuli" *Mol. Gen. Genet.*, 218:315-22 (1989).

Xu et al., "Characterization of a rice gene family encoding root-specific proteins" *Plant Mol. Biol.* 27:237 (1995).

Yamada et al. "A family of transcripts encoding water channel proteins: tissue-specific expression in the common ice plant" *Plant Cell*, 7:1129-42 (1995).

Yamamoto et al., "Characterization of *cis*-Acting sequences regulating root-specific gene expression in Tobacco" *Plant Cell*, 3:371 (1991).

Yi et al. "Auxin and brassinosteroid differentially regulate the expression of three members of the 1-aminocyclopropane-1-carboxylate synthase gene family in mung bean (*Vigna radiata* L.)" *Plant Mol. Biol.*, 41:443-54 (1999).

Zoe et al. "Thermal asymmetric interlaced PCR amplification YAC insert end fragments for chromosome walking in *Plasmodium falciparum* and other A/T-rich genomes" *BioTechniques*, 27(2):240-248 (1999).

GenBank Accession No. AB01919226, dated Feb. 14, 2004, 30 pages.

Sato et al. "Structural analysis of *Arabidopsis thaliana* chromosome 5.X. sequence features of the regions of 3,076,755 bp covered by sixty P1 and TAC Clones" *DNA Research*, 7(31):31-63 (2000).

Score: Search Results Details for Application 11414142, document printed from the Internet on Aug. 13, 2007, 7 pages.

* cited by examiner

US 7,598,367 B2

EARLY LIGHT-INDUCED PROTEIN PROMOTERS

RELATED APPLICATIONS

This application is a continuation-in-part of U.S. patent application Ser. No. 11/172,703 filed Jun. 30, 2005, now U.S. Pat. No. 7,214,789 the entire contents of which are hereby incorporated by reference.

INCORPORATION-BY-REFERENCE & TEXT

The material on the accompanying diskette is hereby incorporated by reference into this application. The accompanying diskette contain one file, 60351877.txt, which was created on Apr. 21, 2006. The file named 60351877.txt is 2 KB. The file can be accessed using Microsoft Word on a computer that uses Windows OS.

TECHNICAL FIELD

The present invention relates to promoters and promoter control elements that are useful for modulating transcription of a desired polynucleotide. In order to modulate in vivo and in vitro transcription of a polynucleotide, such promoters and promoter control elements can be included in polynucleotide constructs, expression cassettes, vectors or inserted into the chromosome or exist in the plant cell as an exogenous element. Host cells with polynucleotides comprising the promoters and promoter control elements of the present invention which have desired traits or characteristics resulting therefrom are also a part of the invention. This includes plant cells and plants regenerated therefrom.

BACKGROUND

This invention relates to the field of biotechnology and in particular to specific promoter sequences and promoter control element sequences which are useful for the transcription of polynucleotides in a host cell or transformed host organism.

One of the primary goals of biotechnology is to obtain organisms such as plants, mammals, yeast and prokaryotes that have particular desired characteristics or traits. Examples of these characteristics or traits abound and in plants may include, for example, virus resistance, insect resistance, herbicide resistance, enhanced stability, enhanced biomass, enhanced yield or additional nutritional value.

Recent advances in genetic engineering have enabled researchers in the field to incorporate polynucleotide sequences into host cells to obtain the desired qualities in the organism of choice. This technology permits one or more polynucleotides from a source different than the organism of choice to be transcribed by the organism of choice. If desired, the transcription and/or translation of these new polynucleotides can be modulated in the organism to exhibit a desired characteristic or trait. Alternatively, new patterns of transcription and/or translation of polynucleotides endogenous to the organism can be produced. Both approaches can be used at the same time.

SUMMARY

The present invention is directed to isolated polynucleotide sequences that comprise promoters and promoter control elements from plants, especially *Arabidopsis thaliana*, and other promoters and promoter control elements that function in plants.

It is an object of the present invention to provide isolated polynucleotides that are promoter sequences. These promoter sequences comprise, for example,
(1) a polynucleotide having the nucleotide sequence set forth in SEQ ID NO:1 or a fragment thereof, and
(2) a polynucleotide having a nucleotide sequence having at least 80% sequence identity to the sequence set forth in SEQ ID NO:1 or a fragment thereof.

Promoter or promoter control element sequences of the present invention are capable of modulating preferential transcription.

In another embodiment, the present promoter control elements are capable of serving as or fulfilling the function of, for example, a core promoter, a TATA box, a polymerase binding site, an initiator site, a transcription binding site, an enhancer, an inverted repeat, a locus control region, or a scaffold/matrix attachment region.

It is yet another object of the present invention to provide a polynucleotide that includes at least a first and a second promoter control element. The first promoter control element is a promoter control element sequence as discussed above and the second promoter control element is heterologous to the first control element. Moreover, the first and second control elements are operably linked. Such promoters may modulate transcript levels preferentially in a tissue or under particular conditions.

In another embodiment, the present isolated polynucleotide comprises a promoter or a promoter control element as described above, wherein the promoter or promoter control element is operably linked to a polynucleotide to be transcribed.

In another embodiment of the present vector, the promoter and promoter control elements of the instant invention are operably linked to a heterologous polynucleotide that is a regulatory sequence.

It is another object of the present invention to provide a host cell comprising an isolated polynucleotide or vector as described above or a fragment thereof. Host cells include, for instance, bacterial, yeast, insect cells, mammalian cells and plant cells. The host cell can comprise a promoter or promoter control element exogenous to the genome. Such a promoter can modulate transcription in cis- and in trans-.

In yet another embodiment, the present host cell is a plant cell capable of regenerating into a plant.

It is yet another embodiment of the present invention to provide a plant comprising an isolated polynucleotide or vector described above.

It is another object of the present invention to provide a method of modulating transcription in a sample that contains either a cell-free system of transcription or a host cell. This method comprises providing a polynucleotide or vector according to the present invention as described above and contacting the sample of the polynucleotide or vector with conditions that permit transcription.

In another embodiment of the present method, the polynucleotide or vector preferentially modulates
(a) constitutive transcription,
(b) stress induced transcription,
(c) light induced transcription,
(d) dark induced transcription,
(e) leaf transcription,
(f) root transcription,
(g) stem or shoot transcription,
(h) silique or seed transcription,
(i) callus transcription,
(j) flower transcription,
(k) immature bud and inflorescence-specific transcription (l) senescence induced transcription, or
(m) germination transcription.

Other and further objects of the present invention will be made clear or become apparent from the following description.

BRIEF DESCRIPTION OF THE TABLE

Table 1 consists of the Expression Report for a promoter of the invention and provides the nucleotide sequence for the promoter as well as details for GFP expression driven by the nucleic acid promoter sequence as observed in transgenic plants. The results are presented as summaries of the spatial expression, which provide information as to gross and/or specific expression in various plant organs and tissues. The observed expression pattern is also presented, which gives details of expression during different generations or different developmental stages within a generation. Additional information is provided regarding the associated gene, the GenBank reference, the source organism of the promoter and the vector and marker genes used for the construct. The following symbols are used consistently throughout the Table:

T1: First generation transformant
T2: Second generation transformant
T3: Third generation transformant
(L): low expression level
(M): medium expression level
(H): high expression level Each row of the table begins with heading of the data to be found in the section. The following provides a description of the data to be found in each section:

| Heading in Table 1 | Description |
|---|---|
| Promoter Expression Report | Identifies the particular promoter report |
| Promoter tested in | Identifies the organism used for analysis |
| Spatial expression summary: | Identifies the organs and tissues where expression was observed and estimates the strength of expression |
| Observed expression pattern: | Presents expression pattern observed for various generations of plants and developmental stages |
| Expected expression pattern: | Identifies the pattern expected from other experiments |
| Selection Criteria: | Provides details on cloning the polynucleotide |
| Gene: | Provides information concerning the gene modulated by the promoter |
| GenBank: | This field gives the Locus Number of the gene as well as the accession number. |
| Source Promoter Organism: | Identifies the organism from which the promoter was cloned. |
| Vector: | Identifies the vector into which the promoter was cloned. |
| Marker Type: | Identifies the type of marker linked to the promoter. The marker is used to determine patterns of gene expression in plant tissue. |
| Generation screened: ☐T1 Mature ☐T2 Seedling ☐T2 Mature ☐T3 Seedling | Identifies the plant generation(s) used in the screening process. T1 plants are those plants subjected to the transformation event while the T2 generation plants are from the seeds collected from the T1 plants and T3 plants are from the seeds of T2 plants. |
| Plant Expression | Identifies the generation and developmental stage of the plants analyzed |
| Events Screened Events Expressing | Provides the number of independent transformation events analyzed and the number which expressed the marker gene |
| GFP Expression Detected | This section lists the various organs analyzed and, where expression was observed, indicates the strength of the expression |
| X in the . . . | This field summarizes the expression pattern from digital images of the cells |
| Promoter Utility: | Identifies a specific function or functions that can be modulated using the promoter cDNA. |
| Trait-Subtrait Area: | Provides information as to what agronomic traits could be altered |
| Construct: | Provides the Ceres identifier number for the construct |
| Promoter Candidate I.D.: | Provides the Ceres identifier number for the promoter isolated |
| cDNA ID: | Provides the Ceres identifier number associated with the cDNA that corresponds to the endogenous cDNA sequence of the promoter. |
| T1 lines expressing (T2 seed): | Provides the identifier numbers for the events analyzed |

-continued

| Heading in Table 1 | Description |
|---|---|
| Sequence | Provides the nucleotide sequence for the promoter described in the report |

DETAILED DESCRIPTION

Definitions

Core Promoter: This is the minimal stretch of contiguous DNA sequence that is sufficient to direct accurate initiation of transcription by the RNA polymerase II machinery (for review see: Struhl, 1987, *Cell* 49:295-297; Smale, 1994, In *Transcription: Mechanisms and Regulation* (eds. R. C. Conaway and J. W. Conaway), pp. 63-81/Raven Press, Ltd., New York; Smale, 1997, *Biochim. Biophys. Acta* 1351:73-88; Smale et al., 1998, *Cold Spring Harb. Symp. Quant. Biol.* 58:21-31; Smale, 2001, *Genes & Dev.* 15:2503-2508; Weis and Reinberg, 1992, *FASEB J.* 6:3300-3309; Burke et al., 1998, *Cold Spring Harb. Symp. Quant. Biol.* 63:75-82). There are several sequence motifs, including the TATA box, initiator (Inr), TFIIB recognition element (BRE) and downstream core promoter element (DPE), that are commonly found in core promoters. Not all of these elements, however, occur in all promoters.

Endogenous: The term "endogenous" within the context of the current invention refers to any polynucleotide, polypeptide or protein sequence which is a natural part of a cell or organism regenerated from said cell. In the context of a promoter, the term "endogenous coding region" or "endogenous cDNA" refers to the coding region that is naturally operably linked to the promoter.

Enhancer/Suppressor: An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

Exogenous: As referred to within, "exogenous" is any polynucleotide, polypeptide or protein sequence that is introduced into a host cell or organism regenerated from said host cell by any means other than by a sexual cross. Examples of means by which this can be accomplished are described below and include *Agrobacterium*-mediated transformation (of dicots—e.g. Salomon et al. *EMBO J.* 3:141 (1984); Herrera-Estrella et al., *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 (1990)), electroporation, in planta techniques and the like. The term "exogenous" as used herein is also intended to encompass inserting a naturally found element into a non-naturally found location.

Heterologous sequences: "Heterologous sequences" are those that are not operatively linked or are not contiguous to each other in nature. For example, a promoter from corn is considered heterologous to an *Arabidopsis* coding region sequence. Also, a promoter from a gene encoding a growth factor from corn is considered heterologous to a sequence encoding the corn receptor for the growth factor. Regulatory element sequences, such as UTRs or 3' end termination sequences that do not originate in nature from the same gene as the coding sequence, are considered heterologous to said coding sequence. Elements operatively linked in nature and contiguous to each other are not heterologous to each other.

Homologous: In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

Inducible Promoter: An "inducible promoter" in the context of the current invention refers to a promoter the activity of which is influenced by certain conditions such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme which is induced by dehydration, abscissic acid and sodium chloride (Hwang and Goodman, *Plant J.* 8:37 (1995)). Examples of environmental conditions that may affect transcription by inducible promoters include anaerobic conditions, elevated temperature, the presence or absence of a nutrient or other chemical compound and/or the presence of light.

Modulate Transcription Level: As used herein, the phrase "modulate transcription" describes the biological activity of a promoter sequence or promoter control element. Such modulation includes, without limitation, up- and down-regulation of initiation of transcription, rate of transcription and/or transcription levels.

Operable Linkage: An "operable linkage" is a linkage in which a promoter sequence or promoter control element is connected to a polynucleotide sequence(s) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoded by the polynucleotide and if the nature of the linkage between the two DNA sequences does not (1) result in the introduction of a frame-shift mutation, (2) interfere with the ability of the promoter sequence to direct the expression of the protein, antisense RNA or ribozyme or (3) interfere with the ability of the DNA template to be transcribed. Thus, a promoter sequence would be operably linked to a polynucleotide sequence if the promoter was capable of effecting transcription of that polynucleotide sequence.

Percentage of sequence identity: "Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Adv. Appl. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci.* (*USA*) 85:2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

Preferential Transcription: "Preferential transcription" is defined as transcription that occurs in a particular pattern of cell types or developmental times or in response to specific stimuli or combination thereof. Non-limiting examples of preferential transcription include: high transcript levels of a desired sequence in root tissues; detectable transcript levels of a desired sequence in certain cell types during embryogenesis; and low transcript levels of a desired sequence under drought conditions. Such preferential transcription can be determined by measuring initiation, rate, and/or levels of transcription.

Promoter: A "promoter" is a DNA sequence that directs the transcription of a polynucleotide. Typically a promoter is located in the 5' region of a polynucleotide to be transcribed. More typically, promoters are defined as the region upstream of the first exon. The promoters of the invention comprise at least a core promoter as defined above. Additionally, the promoter may also include at least one control element such as an upstream element. Such elements include UARs and optionally, other DNA sequences that affect transcription of a polynucleotide such as a synthetic upstream element.

Promoter Control Element: The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats.

Regulatory Sequence: The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

Related Sequences: "Related sequences" refer to either a polypeptide or a nucleotide sequence that exhibits some degree of sequence similarity with a reference sequence.

Specific Promoters: In the context of the current invention, "specific promoters" refers to a subset of promoters that have a high preference for modulating transcript levels in a specific tissue or organ or cell and/or at a specific time during development of an organism. By "high preference" is meant at least 3-fold, preferably 5-fold, more preferably at least 10-fold still more preferably at least 20-fold, 50-fold or 100-fold increase in transcript levels under the specific condition over the transcription under any other reference condition considered. Typical examples of temporal and/or tissue or organ specific promoters of plant origin that can be used with the polynucleotides of the present invention are: PTA29, a promoter which is capable of driving gene transcription specifically in tapetum and only during anther development (Koltunow et al., *Plant Cell* 2:1201 (1990); RCc2 and RCc3 promoters that direct root-specific gene transcription in rice (Xu et al., *Plant Mol. Biol.* 27:237 (1995); and TobRB27, a root-specific promoter from tobacco (Yamamoto et al., *Plant Cell* 3:371 (1991)). Examples of tissue-specific promoters under developmental control include promoters that initiate transcription only in certain tissues or organs, such as root, ovule, fruit, seeds, or flowers. Other specific promoters include those from genes encoding seed storage proteins or the lipid body membrane protein, oleosin. A few root-specific promoters are noted above. See also "Preferential transcription".

Suppressor: See "Enhancer/Suppressor"

Transgenic plant: A "transgenic plant" is a plant having one or more plant cells that contain at least one exogenous polynucleotide introduced by recombinant nucleic acid methods.

Upstream Activation Region (UAR): An "Upstream Activation Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

Untranslated region (UTR): A "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

Variant: The term "variant" is used herein to denote a polynucleotide molecule that differs from others of its kind in some way. For example, polynucleotide variants can consist of changes that add or delete a specific UTR or exon sequence. It will be understood that there may be sequence variations within sequence or fragments used or disclosed in this application. Preferably, variants will be such that the sequences have at least 80%, preferably at least 90%, 95%, 97%, 98%, or 99% sequence identity. Variants preferably measure the primary biological function of the native polypeptide or protein or polynucleotide.

Introduction

The polynucleotides of the invention comprise promoters and promoter control elements that are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:

(a) antisense;

(b) ribozymes;

(c) coding sequences; or (d) fragments thereof.

The promoter also can modulate transcription in a host genome in cis- or in trans-.

In an organism such as a plant, the promoters and promoter control elements of the instant invention are useful to produce preferential transcription which results in a desired pattern of transcript levels in particular cells, tissues or organs or under particular conditions.

Identifying and Isolating Promoter Sequences of the Invention

The promoters and promoter control elements of the present invention include the promoter set forth in SEQ ID NO:1, which was identified from *Arabidopsis thaliana*. Additional promoter sequences encompassed by the invention can be identified as described below.

(1) Cloning Methods

Isolation from genomic libraries of polynucleotides comprising the sequences of the promoters and promoter control elements of the present invention is possible using known techniques.

For example, polymerase chain reaction (PCR) can amplify a desired polynucleotide utilizing primers designed from the sequence set forth in SEQ ID NO:1. Polynucleotide libraries comprising genomic sequences can be constructed according to Sambrook et al., *Molecular Cloning: A Laboratory Manual*, 2$^{nd}$ Ed. (1989) Cold Spring Harbor Press, Cold Spring Harbor, N.Y., for example.

Other procedures for isolating polynucleotides comprising the promoter sequences of the invention include, without limitation, tail-PCR. See, for example, Liu et al. (1995) *Plant J.* 8(3):457-463; Liu et al. (1995) *Genomics* 25:674-681; Liu et al. (1993) *Nucl. Acids Res.* 21(14):3333-3334; Zoe et al. (1999) *BioTechniques* 27(2):240-248; and *PCR Protocols: A Guide to Methods and Applications*, (1990) Academic Press, Inc.

(2) Chemical Synthesis

Promoters and promoter control elements described herein can be chemically synthesized according to techniques in common use. See, for example, Beaucage et al. (1981) *Tet. Lett.* 22:1859 and U.S. Pat. No. 4,668,777.

Such chemical oligonucleotide synthesis can be carried out using commercially available devices, such as Biosearch 4600 or 8600 DNA synthesizer by Applied Biosystems, a division of Perkin-Elmer Corp. (Foster City, Calif., USA) and Expedite by Perceptive Biosystems (Framingham, Mass., USA).

Oligonucleotides can be synthesized and then ligated together to construct the desired polynucleotide.

Isolating Related Promoter Sequences

Included in the present invention are promoters and promoter control elements that are related to those set forth in SEQ ID NO:1. Such related sequences can be isolated using (a) nucleotide sequence identity, (b) coding sequence identity or (c) common function or gene products.

Relatives can include both naturally occurring promoters and non-natural promoter sequences. Non-natural related promoters include nucleotide substitutions, insertions or deletions of naturally-occurring promoter sequences that do not substantially affect transcription modulation activity. For example, the binding of relevant DNA binding proteins can still occur with the non-natural promoter sequences and promoter control elements of the present invention.

Polynucleotides representing changes to the nucleotide sequence by insertion of additional nucleotides, changes to the identity of relevant nucleotides, including use of chemically-modified bases or deletion of one or more nucleotides, are considered encompassed by the present invention.

Relatives Based on Nucleotide Sequence Identity

Included in the present invention are promoters exhibiting nucleotide sequence identity to the sequence set forth in SEQ ID NO:1.

Typically, such related promoters exhibit at least 80% sequence identity, preferably at least 85%, more preferably at least 90%, and most preferably at least 95%, even more preferably, at least 96%, 97%, 98% or 99% sequence identity compared to the sequence set forth in SEQ ID NO:1. Such sequence identity can be calculated by the algorithms and computers programs described above.

Usually, such sequence identity is exhibited in an alignment region that is at least 75% of the length of the sequence set forth in SEQ ID NO:1; more usually at least 80%; more usually, at least 85%, more usually at least 90%, and most usually at least 95%, yet even more usually, at least 96%, 97%, 98% or 99% of the length of the sequence set forth in SEQ ID NO:1.

The percentage of the alignment length is calculated by counting the number of bases of the sequence in the region of strongest alignment, e.g. a continuous region of the sequence that contains the greatest number of bases that are identical to the bases between two sequences that are being aligned. The number of bases in the region of strongest alignment is divided by the total base length of the sequence set forth in SEQ ID NO:1.

These related promoters generally exhibit similar preferential transcription as the promoter set forth in SEQ ID NO:1.

Construction of Polynucleotides

Naturally occurring promoters that exhibit nucleotide sequence identity to the sequence set forth in SEQ ID NO:1 can be isolated using the techniques as described above.

Non-natural promoter variants of the sequence set forth in SEQ ID NO:1 can be constructed using cloning methods that incorporate the desired nucleotide variation. For example, see Ho et al. (1989) *Gene* 77:51-59, which describes a site directed mutagenesis procedure using PCR.

Any related promoter showing sequence identity to the sequence set forth in SEQ ID NO:1 can be chemically synthesized as described above.

Also, the present invention includes non-natural promoters that exhibit the above sequence identity to the sequence set forth in SEQ ID NO:1.

The promoters and promoter control elements of the present invention may also be synthesized with 5' or 3' extensions to facilitate additional manipulation, for instance.

Testing of Polynucleotides

Polynucleotides of the invention can be tested for activity by cloning a sequence into an appropriate vector, transforming plants with the construct and assaying for marker gene expression. Recombinant DNA constructs can be prepared which comprise the polynucleotide sequences of the invention inserted into a vector suitable for transformation of plant cells. The construct can be made using standard recombinant DNA techniques (Sambrook et al. 1989) and can be introduced to the species of interest by *Agrobacterium*-mediated transformation or by other means of transformation as referenced below.

The vector backbone can be any of those typical in the art such as plasmids, viruses, artificial chromosomes, BACs, YACs and PACs.

Typically, the construct comprises a vector containing a sequence of the present invention operationally linked to any marker gene. A polynucleotide can be identified as a promoter by the expression of the marker gene. Although many marker genes can be used, Green Fluorescent Protein (GFP) is preferred. The vector may also comprise a marker gene that confers a selectable phenotype on plant cells. The marker may encode biocide resistance, particularly antibiotic resistance, such as resistance to kanamycin, G418, bleomycin, hygromycin or herbicide resistance, such as resistance to chlorosulfuron or phosphinotricin. Vectors can also include origins of replication, scaffold attachment regions (SARs), markers, homologous sequences, introns, etc.

Promoter Control Elements of the Invention

The promoter control elements of the present invention include those that comprise a sequence set forth in SEQ ID NO:1. Typically, the fragment size is no smaller than 8 bases; more typically, no smaller than 12; more typically, no smaller than 15 bases; more typically, no smaller than 20 bases; more typically, no smaller than 25 bases; even more typically, no more than 30, 35, 40 or 50 bases.

Usually, the fragment size is no larger than 1 kb; more usually, no larger than 800 bases; more usually, no larger than 500 bases; even more usually, no more than 250, 200, 150 or 100 bases.

Promoter Control Element Configuration

Promoters are generally modular in nature. Promoters can consist of a basal promoter which functions as a site for assembly of a transcription complex comprising an RNA polymerase, for example RNA polymerase II. The promoter might also contain one or more promoter control elements such as the elements discussed above. These additional control elements may function as binding sites for additional transcription factors that have the function of modulating the level or transcription with respect to tissue specificity, of transcriptional responses to particular environmental or nutritional factors and the like.

One type of promoter control element is a polynucleotide sequence representing a binding site for proteins. Typically, within a particular functional module, protein binding sites constitute regions of 5 to 60, preferably 10 to 30, more preferably 10 to 20 nucleotides. Within such binding sites, there are typically 2 to 6 nucleotides which specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins and/or a plurality of sites can bind the same protein. Both types of elements may be combined in a region of 50 to 1,000 base pairs.

Non-Natural Control Elements

Non-natural control elements can be constructed by inserting, deleting or substituting nucleotides into the promoter control elements described above. Such control elements are capable of transcription modulation that can be determined using any of the assays described above.

Constructing Promoters with Control Elements (1) Combining Promoters and Promoter Control Elements The promoter polynucleotides and promoter control elements of the present invention, both naturally occurring and synthetic, can be combined with each other to produce the desired preferential transcription. In addition, the polynucleotides of the invention can be combined with other known sequences to generate promoters useful for modulating, for example, tissue-specific transcription or condition-specific transcription. Such preferential transcription can be determined using the techniques or assays described above.

(2) Number of Promoter Control Elements

Promoters can contain any number of control elements. For example, a promoter can contain multiple transcription binding sites or other control elements. One element may confer tissue or organ specificity, another element may limit transcription to specific time periods, etc. Typically, promoters will contain at least a basal or core promoter as described above. Any additional element can be included as desired. For example, a fragment comprising a basal or "core" promoter can be fused with another fragment with any number of additional control elements.

(3) Other Promoters

The following are promoters that are induced under stress conditions and can be combined with those of the present invention: ldh1 (oxygen stress, tomato see Germain and Ricard (1997) *Plant Mol. Biol.* 35:949-54), ci7 (cold stress, potato, see Kirch et al. (1997) *Plant Mol. Biol.* 33:897-909), and Bz2 (heavy metals, maize, see Marrs and Walbot (1997) *Plant Physiol.* 113:93-102).

In addition, the following promoters are examples those induced by the presence or absence of light and can be used in combination with those of the present invention: Topoisomerase II (pea, see Reddy et al. (1999) *Plant Mol. Biol.* 41:125-37), chalcone synthase (soybean, see Wingender et al. (1989) *Mol. Gen. Genet.* 218:315-22), PHYA (*Arabidopsis*, see Canton and Quail (1999) *Plant Physiol.* 121:1207-16), PRB-1b (tobacco, see Sessa et al. (1995) *Plant Mol. Biol.* 28:537-47) and Ypr10 (common bean, see Walter et al. (1996) *Eur. J. Biochem.* 239:281-93).

The promoters and control elements of the following genes can be used in combination with the present invention to confer tissue specificity: for roots MipB (iceplant, Yamada et al. (1995) *Plant Cell* 7:1129-42) and SUCS (root nodules, broadbean, Kuster et al. (1993) *Mol. Plant Microbe Interact.* 6:507-14), for leaves OsSUT1 (rice, Hirose et al. (1997) *Plant Cell Physiol.* 38:1389-96), for siliques Msg (soybean, Stromvik et al. (1999) *Plant Mol. Biol.* 41:217-31) and for inflorescence cell (*Arabidopsis*, Shani et al. (1997) *Plant Mol. Biol.* 34(6):837-42) and ACT11 (*Arabidopsis*, Huang et al. (1997) *Plant Mol. Biol.* 33:125-39).

Still other promoters are affected by hormones or participate in specific physiological processes, which can be used in combination with those of present invention. Some examples are the ACC synthase gene that is induced differently by ethylene and brassinosteroids (mung bean, Yi et al. (1999) *Plant Mol. Biol.* 41:443-54), the TAPG1 gene that is active during abscission (tomato, Kalaitzis et al. (1995) *Plant Mol.*

*Biol.* 28:647-56) and the 1-aminocyclopropane-1-carboxylate synthase gene (carnation, Jones et al. (1995) *Plant Mol. Biol.* 28:505-12).

Vectors

Vectors are a useful component of the present invention. In particular, vectors can deliver the present promoters and/or promoter control elements to a cell. For the purposes of this invention, such delivery ranges from randomly introducing the promoter or promoter control element alone into a cell to integrating the vector containing the promoter or promoter control element into a cell's genome. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are preferred vectors for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al. (1985) *Nature* 317:741-744; Gordon-Kamm et al. (1990) *Plant Cell* 2:603-618; and Stalker et al. (1988) *Science* 242:419-423). Other marker genes exist which provide hormone responsiveness.

(1) Modification of Transcription by Promoters and Promoter Control Elements

The promoter or promoter control element of the present invention may be operably linked to a polynucleotide to be transcribed.

The promoter or promoter control element need not be linked, operably or otherwise, to a polynucleotide to be transcribed before being inserted into a genome. For example, the promoter or promoter control element can be inserted into the genome in front of a polynucleotide already present therein. Here, the promoter or promoter control element modulates the transcription of a polynucleotide that was already present in the genome. This polynucleotide may be native to the genome or inserted at an earlier time.

Alternatively, the promoter or promoter control element can simply be inserted into a genome or maintained extrachromosomally as a way to divert the transcription resources of the system to itself. See, for example, Vaucheret et al. (1998) *Plant J.* 16:651-659. This approach may be used to down-regulate the transcript levels of a group of polynucleotide(s).

(2) Polynucleotide to be Transcribed

The nature of the polynucleotide to be transcribed is not limited. Specifically, the polynucleotide may include sequences that will have activity as RNA as well as sequences that result in a polypeptide product. These sequences may include, but are not limited to antisense sequences, ribozyme sequences, spliceosomes, amino acid coding sequences and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to secondary product metabolism, amino acid synthesis, seed protein storage, oil development, pest defense and nitrogen usage. Some examples of genes, transcripts, peptides or polypeptides participating in these processes which can be modulated by the present invention: are tryptophan decarboxylase (tdc), strictosidine synthase (strl), dihydrodipicolinate synthase (DH-DPS), aspartate kinase (AK), 2S albumin, alpha-, beta-, and gamma-zeins, ricinoleate, 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon that encodes the first methionine. Thus, when constructing a recombinant polynucleotide for expressing a protein product according to the present invention, it is preferable to ensure that no intervening codons encoding a methionine are contained within the linkage between the polynucleotide to be transcribed and the 3' portion of the promoter.

The vector of the present invention may contain additional components. For example, an origin of replication that allows for replication of the vector in a host cell may be added. In addition, homologous sequences flanking a target location in the genome may be added to allow for site-specific recombination of a specific sequence contained in the vector. T-DNA sequences also allow for insertion of a specific sequence randomly into a target genome.

The vector may also contain a plurality of restriction sites for insertion of the promoter and/or promoter control elements of the present invention as well as any polynucleotide to be transcribed. The vector can additionally contain selectable marker genes. The vector can also contain a transcriptional and translational initiation region and/or a transcriptional and translational termination region that functions in the host cell. The termination region may be native with the transcriptional initiation region, may be native with the polynucleotide to be transcribed or may be derived from another source. Convenient termination regions are available from the Ti-plasmid of *A. tumefaciens*, such as the octopine synthase and nopaline synthase termination regions. See also, Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; Joshi et al. (1987) *Nucleic Acid Res.* 15:9627-9639.

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831 and 5,436,391 and Murray et al. (1989) *Nucleic Acids Res.* 17:477-498.

Additional sequence modifications include elimination of sequences encoding spurious polyadenylation signals, exon intron splice site signals, transposon-like repeats and other such sequences well characterized as deleterious to expression. The G-C content of the polynucleotide may be adjusted to the average levels for a given cellular host, as calculated by reference to known genes expressed in the host cell. The polynucleotide sequence may be modified to avoid hairpin secondary mRNA structures.

A general description of expression vectors and reporter genes can be found in Gruber et al., "Vectors for Plant Transformation", in Methods in Plant Molecular Biology & Biotechnology (1993) Glich et al. eds., pp. 89-119, CRC Press. Moreover GUS expression vectors and GUS gene cassettes are available from Clontech Laboratories, Inc. (Palo Alto, Calif.) while luciferase expression vectors and luciferase gene cassettes are available from Promega Corp. (Madison, Wis.). GFP vectors are available from Aurora Biosciences.

Polynucleotide Insertion into a Host Cell

The polynucleotides according to the present invention can be inserted into a host cell. A host cell includes but is not limited to a plant, mammalian, insect, yeast and prokaryotic cell, preferably a plant cell.

The method of insertion into the host cell genome is chosen based on convenience. For example, the insertion into the host cell genome may either be accomplished by vectors that integrate into the host cell genome or by vectors which exist independent of the host cell genome.

(1) Polynucleotides Autonomous of the Host Genome

The polynucleotides of the present invention can exist autonomously or independent of the host cell genome. Vectors of these types are known in the art and include, for example, certain types of non-integrating viral vectors, autonomously replicating plasmids, artificial chromosomes and the like.

Additionally, in some cases transient expression of a polynucleotide may be desired.

(2) Polynucleotides Integrated into the Host Genome

The promoter sequences, promoter control elements or vectors of the present invention can be transformed into host cells. These transformations can be into protoplasts or isolated cells or intact tissues. Preferably, expression vectors are introduced into intact tissue. General methods of culturing plant tissues are provided for example by Maki et al. ("Procedures for Introducing Foreign DNA into Plants" in Methods in Plant Molecular Biology & Biotechnology (1993) Glich et al. (Eds. pp. 67-88 CRC Press) and by Phillips et al. "Cell-Tissue Culture and In-Vitro Manipulation" in Corn & Corn Improvement, 3rd Edition Sprague et al. (1998) eds. pp. 345-387) American Society of Agronomy Inc.

Methods of introducing polynucleotides into plant tissue include the direct infection or co-cultivation of a plant cell with *Agrobacterium tumefaciens* (Horsch et al. (1985) *Science* 227:1229). Descriptions of *Agrobacterium* vector systems and methods for *Agrobacterium*-mediated gene transfer are provided by Gruber et al. supra.

Alternatively, polynucleotides are introduced into plant cells or other plant tissues using a direct gene transfer method such as microprojectile-mediated delivery, DNA injection, electroporation and the like. More preferably, polynucleotides are introduced into plant tissues using the microprojectile media delivery with the biolistic device. See, for example, Tomes et al., "Direct DNA transfer into intact plant cells via microprojectile bombardment" In: Plant Cell, Tissue and Organ Culture: Fundamental Methods (1995) Gamborg and Phillips eds. Springer Verlag, Berlin.

Integration into the host cell genome also can be accomplished by methods known in the art such as by homologous sequences or T-DNA discussed above or by using the cre-lox system (Vergunst et al. (1998) *Plant Mol. Biol.* 38:393).

Utility

Common Uses

The promoters of the present invention can be used to further understand developmental mechanisms. For example, promoters that are specifically induced during callus formation, somatic embryo formation, shoot formation or root formation can be used to explore the effects of overexpression, repression or ectopic expression of target genes, or for isolation of trans-acting factors.

The vectors of the invention can be used not only for expression of coding regions but may also be used in exon-trap cloning, or promoter trap procedures to detect differential gene expression in various tissues. See Lindsey et al. (1993) "Tagging Genomic Sequences That Direct Transgene Expression by Activation of a Promoter Trap in Plants," *Transgenic Research* 2:3347 and Auch et al. "Exon Trap Cloning: Using PCR to Rapidly Detect and Clone Exons from Genomic DNA Fragments," *Nucleic Acids Research*, 18:674.

Constitutive Transcription

Promoters and control elements providing constitutive transcription are desired for modulation of transcription in most cells of an organism under most environmental conditions. In a plant, for example, constitutive transcription is useful for modulating genes involved in defense, pest resistance, herbicide resistance, etc.

Constitutive up-regulation and down-regulation of transcription are useful for these applications. For instance, genes, transcripts and/or polypeptides that increase defense, pest and herbicide resistance may require constitutive up-regulation of transcription. In contrast, constitutive down-regulation of transcription may be desired to inhibit those genes, transcripts, and/or polypeptides that lower defense, pest and herbicide resistance.

Stress Induced Preferential Transcription

Promoters and control elements providing modulation of transcription under oxidative, drought, oxygen, wound and methyl jasmonate stress are particularly useful for producing host cells or organisms that are more resistant to biotic and abiotic stresses. For example, in a plant modulation of genes, transcripts and/or polypeptides in response to oxidative stress can protect cells against damage caused by oxidative agents such as hydrogen peroxide and other free radicals.

Drought induction of genes, transcripts and/or polypeptides are useful to increase the viability of a plant, for example when water is a limiting factor. In contrast, genes, transcripts and/or polypeptides induced during oxygen stress can help the flood tolerance of a plant.

Examples of some genes involved in stress condition responses are VuPLD1 (drought stress, Cowpea; Pham-Thi et al. (1999) *Plant Mol. Biol.* 1257-65), pyruvate decarboxylase (oxygen stress, rice; Rivosal et al. (1997) *Plant Physiol.* 114 (3):1021-29), and the chromoplast specific carotenoid gene (oxidative stress, *Capsicum*; see Bouvier et al. (1998) *J. Biol. Chem.* 273:30651-59).

Promoters and control elements providing preferential transcription during wounding or that are induced by methyl jasmonate can produce a defense response in host cells or organisms. In a plant, preferential modulation of genes, transcripts and/or polypeptides under such conditions is useful to induce a defense response to mechanical wounding, pest or pathogen attack or treatment with certain chemicals.

Examples include cf9 (viral pathogen, tomato; O'Donnell et al. (1998) *Plant J.* 14(1):137-42), copper amine oxidase (CuAO) induced during ontogenesis and wound healing (wounding, chick-pea; Rea et al. (1998) *FEBS Letters* 437: 177-82), proteinase inhibitor II (wounding, potato; Pena-Cortes et al. (1988) *Planta* 174:84-89), protease inhibitor II (methyl jasmonate, tomato; Farmer and Ryan (1990) *Proc. Natl. Acad. Sci. USA* 87:7713-7716) and two vegetative storage protein genes VspA and VspB (wounding, jasmonic acid and water deficit; soybean; Mason and Mullet (1990) *Plant Cell* 2:569-579).

Up-regulation and down-regulation of transcription are useful for these applications. For instance, genes, transcripts and/or polypeptides that increase oxidative, flood or drought tolerance may require up-regulation of transcription. In contrast, transcriptional down-regulation may be desired to inhibit those genes, transcripts and/or polypeptides that lower such tolerance.

Light Induced Preferential Transcription

Promoters and control elements providing preferential transcription when induced by light exposure can be utilized to modulate growth, metabolism and development; to increase drought tolerance; and to decrease damage from light stress for host cells or organisms. In a plant, modulation of genes, transcripts and/or polypeptides in response to light is useful (1) to increase the photosynthetic rate;
(2) to increase storage of certain molecules in leaves or green parts only, e.g. silage with high protein or starch content;
(3) to modulate production of exogenous compositions in green tissue, e.g. certain feed enzymes;
(4) to induce growth or development, such as fruit development and maturity, during extended exposure to light;
(5) to modulate guard cells to control the size of stomata in leaves to prevent water loss; or
(6) to induce accumulation of beta-carotene to help plants cope with light induced stress.

Examples include: abscisic acid insensitive3 (ABI3) (dark-grown *Arabidopsis* seedlings, Rohde et al. (2000) *Plant Cell* 12: 35-52), and asparagine synthetase (pea root nodules, Tsai and Coruzzi, (1990) *EMBO J.* 9:323-32).

Up-regulation and down-regulation of transcription are useful for these applications. For instance, genes, transcripts and/or polypeptides that increase drought or light tolerance may require up-regulation of transcription. In contrast, transcriptional down-regulation may be desired to inhibit those genes, transcripts and/or polypeptides that lower such tolerance.

Dark Induced Preferential Transcription

Promoters and control elements providing preferential transcription when induced by dark or decreased light intensity or decreased light exposure time can be utilized to time growth, metabolism and development and to modulate photosynthesis capabilities for host cells or organisms. In a plant, modulation of genes, transcripts and/or polypeptides in response to dark is useful (1) to induce growth or development, such as fruit development and maturity, despite lack of light;
(2) to modulate genes, transcripts and/or polypeptides active at night or on cloudy days; or
(3) to preserve the plastid ultra structure present at the onset of darkness.

Up-regulation and down-regulation of transcription are useful for these applications. For instance, genes, transcripts and/or polypeptides that increase growth and development may require up-regulation of transcription. In contrast, transcriptional down-regulation may be desired to inhibit those genes, transcripts and/or polypeptides that modulate photosynthesis capabilities.

Leaf Preferential Transcription

Promoters and control elements providing preferential transcription in a leaf can modulate growth, metabolism and development or modulate energy and nutrient utilization in host cells or organisms. In a plant, preferential modulation of genes, transcripts and/or polypeptides in a leaf is useful (1) to modulate leaf size, shape, and development;
(2) to modulate the number of leaves; or
(3) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a leaf and to redirect it to the fruit instead, for instance.

Root Preferential Transcription

Promoters and control elements providing preferential transcription in a root can modulate growth, metabolism, development, nutrient uptake, nitrogen fixation or modulate energy and nutrient utilization in host cells or organisms. In a plant, for example, preferential modulation of genes, transcripts, and/or polypeptides in a leaf, is useful (1) to modulate root size, shape, and development;
(2) to modulate the number of roots, or root hairs;
(3) to modulate mineral, fertilizer, or water uptake;
(4) to modulate transport of nutrients; or
(5) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit nutrient usage in a root and to redirect it to the leaf instead, for instance.

Stem/Shoot Preferential Transcription

Promoters and control elements providing preferential transcription in a stem or shoot can modulate growth, metabolism and development or modulate energy and nutrient utilization in host cells or organisms. In a plant, preferential modulation of genes, transcripts and/or a polypeptide in a stem or shoot is useful (1) to modulate stem/shoot size, shape, and development; or
(2) to modulate energy or nutrient usage in relation to other organs and tissues.

Up-regulation and down-regulation of transcription are useful for these applications. For instance, genes, transcripts and/or polypeptides that increase growth may require up-regulation of transcription. In contrast, transcriptional down-regulation may be desired to inhibit energy usage in a stem/shoot and to redirect it to the fruit instead, for instance.

Fruit and Seed Preferential Transcription

Promoters and control elements providing preferential transcription in a silique or fruit can time growth, development, or maturity; or modulate fertility; or modulate energy and nutrient utilization in host cells or organisms. In a plant preferential modulation of genes, transcripts and/or polypeptides in a fruit is useful (1) to modulate fruit size, shape, development, and maturity;
(2) to modulate the number of fruit or seeds;
(3) to modulate seed shattering;
(4) to modulate components of seeds, such as, storage molecules, starch, protein, oil, vitamins, anti-nutritional components, such as phytic acid;
(5) to modulate seed and/or seedling vigor or viability;
(6) to incorporate exogenous compositions into a seed, such as lysine rich proteins;

(7) to permit similar fruit maturity timing for early and late blooming flowers; or (8) to modulate energy or nutrient usage in relation to other organs and tissues.

Up-regulation and down-regulation of transcription are useful for these applications. For instance, genes, transcripts, and/or polypeptides that increase growth may require up-regulation of transcription. In contrast, transcriptional down-regulation may be desired to inhibit late fruit maturity, for instance.

Callus Preferential Transcription

Promoters and control elements providing preferential transcription in a callus can be useful for modulating transcription in dedifferentiated host cells. In a plant transformation, for example, preferential modulation of genes or transcript in callus is useful to modulate transcription of a marker gene, which can facilitate selection of cells that are transformed with exogenous polynucleotides.

Up-regulation and down-regulation of transcription are useful for these applications. For instance, genes, transcripts and/or polypeptides that increase marker gene detectability may require up-regulation of transcription. In contrast, transcriptional down-regulation may be desired to increase the ability of the calluses to differentiate, for instance.

Flower Specific Transcription

Promoters and control elements providing preferential transcription in flowers can modulate pigmentation or modulate fertility in host cells or organisms. In a plant, preferential modulation of genes, transcripts and/or polypeptides in a flower is useful (1) to modulate petal color; or (2) to modulate the fertility of pistil and/or stamen.

Up-regulation and down-regulation of transcription are useful for these applications. For instance, genes, transcripts and/or polypeptides that increase pigmentation may require up-regulation of transcription. In contrast, transcriptional down-regulation may be desired to inhibit fertility, for instance.

Immature Bud and Inflorescence Preferential Transcription

Promoters and control elements providing preferential transcription in an immature bud or inflorescence can time growth, development or maturity or modulate fertility or viability in host cells or organisms. In a plant, preferential modulation of genes, transcripts, and/or polypeptides in an immature bud or inflorescence is useful (1) to modulate embryo development, size, and maturity;

(2) to modulate endosperm development, size, and composition;

(3) to modulate the number of seeds and fruits; or (4) to modulate seed development and viability.

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

Senescence Preferential Transcription

Promoters and control elements providing preferential transcription during senescence can be used to modulate cell degeneration, nutrient mobilization and scavenging of free radicals in host cells or organisms. Other types of responses that can be modulated include, for example, senescence associated genes (SAG) that encode enzymes thought to be involved in cell degeneration and nutrient mobilization (*Arabidopsis*; Hensel et al. (1993) *Plant Cell* 5: 553-64).

In a plant, preferential modulation of genes, transcripts and/or polypeptides during senescing is useful to modulate fruit ripening.

Up-regulation and down-regulation of transcription are useful for these applications. For instance, genes, transcripts and/or polypeptides that increase scavenging of free radicals may require up-regulation of transcription. In contrast, transcriptional down-regulation may be desired to inhibit cell degeneration, for instance.

Germination Preferential Transcription

Promoters and control elements providing preferential transcription in a germinating seed can time growth, development or maturity or modulate viability in host cells or organisms. In a plant, preferential modulation of genes, transcripts and/or polypeptides in a germinating seed is useful (1) to modulate the emergence of the hypocotyls, cotyledons and radical; or (2) to modulate shoot and primary root growth and development.

Up-regulation and down-regulation of transcription is useful for these applications. For instance, genes, transcripts and/or polypeptides that increase growth may require up-regulation of transcription. In contrast, transcriptional down-regulation may be desired to decrease endosperm size, for instance.

The invention will be further described in the following examples, which do not limit the scope of the invention described in the claims.

EXAMPLES

The polynucleotide sequences of the present invention were tested for promoter activity using Green Fluorescent Protein (GFP) assays in the following manner.

Approximately 1-2 kb of genomic sequence occurring upstream of the ATG translational start site of the gene of interest was isolated using appropriate primers tailed with BstXI restriction sites. Standard PCR reactions using these primers and genomic DNA were conducted. The resulting product was isolated, cleaved with BstXI and cloned into the BstXI site of an appropriate vector, such as pNewBin-4-HAP1-GFP.

GFP Assay

After transformation, tissues from transgenic plants are dissected by eye or under magnification using INOX 5 grade forceps and placed on a slide with water and coversliped. An attempt is made to record images of observed expression patterns at earliest and latest stages of development of tissues listed below. Specific tissues will be preceded with High (H), Medium (M), Low (L) designations.

| | |
|---|---|
| Flower | Pedicel, receptacle, nectary, sepal, petal, filament, anther, pollen, carpel, style, papillae, vascular, epidermis, stomata, trichome |
| Silique | Stigma, style, carpel, septum, placentae, transmitting tissue, vascular, epidermis, stomata, abscission zone, ovule |
| Ovule | Pre-fertilization: inner integument, outer integument, embryo sac, funiculus, chalaza, micropyle, gametophyte Post-fertilization: zygote, inner integument, outer integument, seed coat, primordial, chalaza, micropyle, early endosperm, mature endosperm, embryo |
| Embryo | Suspensor, preglobular, globular, heart, torpedo, late, mature, provascular, hypophysis, radicle, cotyledons, hypocotyl |
| Stem | epidermis, cortex, vascular, xylem, phloem, pith, stomata, trichome |
| Leaf | Petiole, mesophyll, vascular, epidermis, trichome, primordial, stomata, stipule, margin |

T1 Mature: These are the T1 plants resulting from independent transformation events. These are screened between stage 6.50-6.90 (means the plant is flowering and that 50-90% of the flowers that the plant will make have developed) which is 4-6 weeks of age. At this stage the mature plant possesses flowers, siliques at all stages of development, and fully expanded leaves. We do not generally differentiate between 6.50 and 6.90 in the report but rather just indicate 6.50. The plants are initially imaged under UV with a Leica Confocal microscope. This allows examination of the plants on a global level. If expression is present, they are imaged using scanning laser confocal microscopy.

T2 Seedling: Progeny are collected from the T1 plants giving the same expression pattern and the progeny (T2) are sterilized and plated on agar-solidified medium containing M&S salts. In the event that there was no expression in the T1 plants, T2 seeds are planted from all lines. The seedlings are grown in Percival incubators under continuous light at 22° C. for 10-12 days. Cotyledons, roots, hypocotyls, petioles, leaves, and the shoot meristem region of individual seedlings were screened until two seedlings were observed to have the same pattern. Generally found the same expression pattern was found in the first two seedlings. However, up to 6 seedlings were screened before "no expression pattern" was recorded. All constructs are screened as T2 seedlings even if they did not have an expression pattern in the T1 generation.

T2 Mature: The T2 mature plants were screened in a similar manner to the T1 plants. The T2 seeds were planted in the greenhouse, exposed to selection and at least one plant screened to confirm the T1 expression pattern. In instances where there were any subtle changes in expression, multiple plants were examined and the changes noted in the tables.

T3 Seedling: This was done similar to the T2 seedlings except that only the plants for which we are trying to confirm the pattern are planted.

Image Data

Images are collected by scanning laser confocal microscopy. Scanned images are taken as 2-D optical sections or 3-D images generated by stacking the 2-D optical sections collected in series. All scanned images are saved as TIFF files by imaging software, edited in Adobe Photoshop, and labeled in Powerpoint specifying organ and specific expressing tissues.

Instrumentation:

Microscope
Inverted Leica DM IRB

Fluorescence Filter Blocks:
Blue excitation BP 450-490; long pass emission LP 515.
Green excitation BP 515-560; long pass emission LP 590.

Objectives
HC PL FLUOTAR 5×/0.5
HCPL APO 10×/0.4 IMM water/glycerol/oil
HCPL APO 20×/0.7 IMM water/glycerol/oil
HCXL APO 63×/1.2 IMM water/glycerol/oil Leica TCS SP2 Confocal Scanner
Spectral range of detector optics 400-850 nm.
Variable computer controlled pinhole diameter.
Optical zoom 1-32×.

Four Simultaneous Detectors:
Three channels for collection of fluorescence or reflected light.
One channel for transmitted light detector.

Laser Sources:
Blue Ar 458/5 mW, 476 nm/5 mW, 488 nm/20 mW, 514 nm/20 mW.
Green HeNe 543 nm/1.2 mW
Red HeNe 633 nm/10 mW Results

TABLE 1

Promoter Expression Report #161
Promoter Tested In: *Arabidopsis thaliana*, Wassilewskija (WS) ecotype
Spatial expression summary:

| | |
|---|---|
| Flower | H pedicel H sepal H petal H filament H anther H carpel H style H epidermis H stomata H silique |
| Silique | H style H carpel H transmitting tissue H epidermis H ovule |
| Ovule | Pre-fertilization: L funiculus L outer integument |
| | Post-fertilization: H funiculus H outer integument H seed coat |
| Stem | L vascular L phloem |
| Leaf | L vascular |
| Hypocotyl | H epidermis L vascular |
| Cotyledon | L epidermis |
| Rosette Leaf | L vascular L epidermis |
| Primary Root | H epidermis H cortex H endodermis H vascular H quiescent H root cap H root hairs |

Observed expression pattern:
T1 mature: GFP expression in sepals, petals, stamens and siliques of developing floral buds through to mature flowers. GFP expression throughout all tissues of stamen excluding pollen. GFP expression throughout all tissues of silique excluding stigma. Within ovules, highest GFP expression is at funiculus, outer integument and mature seed coat. GFP expression in vascular tissues of flowers, stems and leaves. In stem, expression in phloem cells within vascular bundle. Expression in guard cells throughout plant.
T2 seedling: High GFP expression throughout epidermal tissues of seedlings. High GFP expression throughout all root cell types decreasing toward elongation zone. GFP is expressed in root cap and meristem cells.
Expected expression pattern: High in siliques

| | |
|---|---|
| Selection Criteria: | Microarray data |
| Gene: | Chlorophyll A-B binding family protein/early light-induced protein |
| GenBank: | NM_113183 *Arabidopsis thaliana* chlorophyll A-B binding family protein/early light-induced protein (ELIP) (At3g22840) mRNA, complete cds gi\|30686801\| |
| Source Promoter Organism: | *Arabidopsis thaliana*, Columbia (Col) ecotype |
| Vector: | pNewbin4-HAP1-GFP |
| Marker Type: | GFP-ER |

TABLE 1-continued

Generation Screened: X T1 Mature  X T2 Seedling  ☐T2 Mature  ☐T3 Seedling
Inductions completed.

| Treatment: | Age: | Gen: | Time points: | Events Screened/Response: | Response: |
|---|---|---|---|---|---|
| 1. Drought | 4 wks | T2 | 8 days no water | 2/0 | No |
| 2. Heat | 7 days | T2 | 2 Hr 42 C. | 3/0 | No |
| | | | 6 Hr 42 C. | 3/0 | No |
| | | | 16 Hrs - Post 42 C. | 3/0 | No |

T1 Mature Plant Expression  Organs/Tissues screened
Events Screened: n = 6      Events Expressing: n = 3
GFP Expression Detected

| | |
|---|---|
| X Flower | H pedicel ☐receptacle ☐nectary H sepal H petal H filament H anther ☐pollen H carpel H style ☐papillae ☐vascular H epidermis H stomata ☐trichome H silique |
| X Silique | ☐stigma H style H carpel ☐septum ☐ placentae H transmitting tissue ☐vascular H epidermis ☐stomata ☐abscission zone H ovule |
| X Ovule | Pre-fertilization: ☐primordia ☐inner integument L outer integument ☐embryo sac L funiculus ☐chalaza ☐micropyle ☐gametophyte Post-fertilization: ☐zygote ☐suspensor ☐ embryo sac H funiculus ☐inner integument H outer integument ☐endothelium H seed coat ☐primordia |
| ☐ Embryo | ☐chalaza ☐micropyle ☐early endosperm ☐mature endosperm ☐embryo ☐suspensor ☐preglobular ☐globular ☐heart ☐torpedo ☐late ☐mature ☐provascular ☐hypophysis ☐radicle ☐cotyledons ☐hypocotyl |
| X Stem | ☐epidermis ☐cortex L vascular ☐xylem L phloem ☐pith ☐stomata ☐trichome |
| X Leaf | ☐petiole ☐mesophyll L vascular ☐epidermis ☐trichome ☐primordia ☐stomata ☐stipule ☐margin |
| ☐ Shoot apical meristem | ☐shoot apical meristem ☐flower primordium |

X Pedicel (Pd) and Stem (Sm) in the inflorescence meristem
X Pedicel (Pd) and flower bud in the inflorescence meristem
X Sepal (Se) in the flower
X Pollen (Po), Petal (Pe) and Stamen (St) in the stamen
X Pollen (Po), Ovule (Ov) and Stigma (Sg) in the pre-fertilized silique
X Stigma (Sg) and Pollen transmitting tract (Tt) in the unfertilized stigma
X Funiculus (Fn) in the pre-fertilized ovule
X Funiculus (Fn) and Chalaza (Ch) in the fertilized ovule
X Funiculus (Fn), Placenta (Pl) and Outer Integument (Oi) in the developing seed
X and Outer Integument (Oi) in the developing seed
X Seed coat (Sc) in the early mature seed
X in the Seed coat (Sc)
X Columella (Cm), Radial wall (Rw) and Starch granule (Sg) in the seed coat
X in the embryo
X Guard cell (Gc), Vasculature (Vs) and Hydathode (Hd) in the Leaf
X in the stem T2 Seedling Expression    Tissues Screened
Events Screened: n = 3    Events Expressing: n = 3
Seedlings expressing/Seedlings screened
Event-01: 3/4
Event-05: 3/6
Event-06: 4/6
☐ Scheduled
GFP Expression Detected

| | |
|---|---|
| X Hypocotyl | H epidermis ☐cortex L vascular ☐xylem ☐phloem ☐stomata |
| X Cotyledon | ☐mesophyll ☐vascular L epidermis ☐margin ☐stomata ☐hydathode |
| X Rosette Leaf | ☐mesophyll L vascular L epidermis ☐trichome ☐petiole ☐primordia ☐stomata ☐stipule ☐margin ☐hydathode |
| X Primary Root | H epidermis ☐trichoblast ☐atrichoblast H cortex H endodermis H vascular ☐xylem ☐phloem ☐pericycle H quiescent ☐columella H root cap H root hairs |
| ☐ Lateral root | ☐epidermis ☐trichoblast ☐atrichoblast ☐cortex ☐endodermis ☐initials ☐flanking cells ☐vascular ☐lateral root cap |
| ☐ Shoot apical meristem | ☐shoot apical meristem |

X in the leaf
X Epidermis (Ep) and Vasculature (Vs) in the leaf
X Epidermis (Ep), Hypocotyl (Hy), Root (Rt) and Vasculature (Vs) in the seedling
X Root apical meristem (RAM) in the root tip Promoter utility
| | |
|---|---|
| Trait Area: | Nutrients, seed yield, water use efficiency |
| Sub-trait Area: | Nitrogen use efficiency, ovule/seed abortion, endosperm cell number/size, endosperm granule number/size, seed enhancement, seed number, harvest index, heat, water potential, drought, moisture stress at seed set |
| Utility: | Among other uses this promoter sequence could be useful to improve: |

Notes: This promoter is strongly differentially regulated under drought conditions and in a number of tissues.
Construct:            PT0623
Promoter candidate I.D:    11768718

TABLE 1-continued

| cDNA I.D: | 23644072 |
|---|---|
| Lines expressing: | PT0623 -01, -05, -06 |

Sequence (SEQ ID NO: 1):
aaagttattgacattttgaaaggaccgtaaatattaccaaaaaactgacg gagttaggatcggccacgtagaaagggacaaagagagaacagtcacggac tcggccagactaagtatgggcctgtctgaatccaaactcagctaagttcc aaaagcataaagagagatgtgtaatgaaatgaacgtattctagaaacgaa agcaatgttatgctttgttttgagccacatgttttttgggagatggagag aatctttttacgttttaacctaacccacttggcacttggccaaaaaag tgagaagaaactgtggcgaatgagtaggccacgccatggactttgttcct tgtccttcaaaagttaaatttatgttatgcgtggggacaatctaagcaac gtggttcctttaaatatcgcagcttcctcttttacactttggagcctac gtgttttgttttggaccggccaaatacacgagtcagtcagtttagaaata atttggatgtccaaaaatcttggagatccaaataaaataattagcatgtt ttagttcataagaatatgaaatgtagataaactgtctatattaattttc catagaattggctttttatcgaggtgatgtacttaatgactttgttgatt actactcgtataacaataaagaatatgatactatgtgagacttataatga atttggtgtgtgttaattaatccagttgaaacagtttaataacaaatcag aataaaaattgtagtaagaaaatttgaacgctgatccttcaacctagata gtgaacctttcaaatactatatgattcacgtgtaatgtttttgaccgttg gttattttgtgtgaactatattaacttatcaatatcgaaaggctaaata agtaaataactaaaagaaagttcaggaaacaactcgacctaatgacctat catttctgatcacccgtcctataaatacatacgtaagatcattcgttact The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

What is claimed is:

1. A recombinant DNA construct comprising a promoter operably linked to a heterologous nucleic acid, said promoter consisting of the nucleotide sequence set forth in SEQ ID NO:1.

2. A transgenic plant comprising the recombinant DNA construct of claim 1.

3. A method of making a plant comprising introducing into a plant the recombinant DNA construct of claim 1.

* * * * *

SEQUENCE LISTING

<160> NUMBER OF SEQ ID NOS: 1

<210> SEQ ID NO 1
<211> LENGTH: 1000
<212> TYPE: DNA
<213> ORGANISM: Arabidopsis thaliana
<220> FEATURE:
<221> NAME/KEY: misc_feature
<222> LOCATION: (1)..(1000)
<223> OTHER INFORMATION: Ceres Promoter PT0623
<220> FEATURE:
<221> NAME/KEY: misc_feature
<222> LOCATION: (1)..(1000)
<223> OTHER INFORMATION: Promoter Candidate ID 11768718

<400> SEQUENCE: 1

```
aaagttattg acattttgaa aggaccgtaa atattaccaa aaaactgacg gagttaggat      60
cggccacgta gaaagggaca agagagaac agtcacggac tcggccagac taagtatggg     120
cctgtctgaa tccaaactca gctaagttcc aaaagcataa agagagatgt gtaatgaaat     180
gaacgtattc tagaaacgaa agcaatgtta tgctttgttt ttgagccaca tgttttggg      240 agatggagag aatctttttt acgttttaa cctaacccac ttggcacttg gccaaaaaag     300
tgagaagaaa ctgtggcgaa tgagtaggcc acgccatgga ctttgttcct tgtccttcaa     360
aagttaaatt tatgttatgc gtggggacaa tctaagcaac gtggttcctt taaatatcgc     420
agcttcctct tttacactt tggagcctac gtgttttgtt ttggaccggc caaatacacg     480
agtcagtcag tttagaaata atttggatgt ccaaaaatct tggagatcca aataaaataa     540
```

```
ttagcatgtt ttagttcata agaatatgaa atgtagataa actgtctata ttaattttc    600 catagaattg gcttttatc gaggtgatgt acttaatgac tttgttgatt actactcgta    660
taacaataaa gaatatgata ctatgtgaga cttataatga atttggtgtg tgttaattaa    720
tccagttgaa acagtttaat aacaaatcag aataaaaatt gtagtaagaa aatttgaacg    780
ctgatccttc aacctagata gtgaacctt caaatactat atgattcacg tgtaatgttt    840
ttgaccgttg gttattttg tgtgaactat attaacttat caatatcgaa aggctaaata    900
agtaaataac taaaagaaag ttcaggaaac aactcgacct aatgacctat catttctgat    960
cacccgtcct ataaatacat acgtaagatc attcgttact                        1000
```